United States Patent [19]

Burress

[11] Patent Number: 4,629,818

[45] Date of Patent: Dec. 16, 1986

[54] AROMATIZATION CATALYST FOR A REFINERY OFF GAS STREAM

[75] Inventor: George T. Burress, Bridgewater, N.J.

[73] Assignee: Mobil Oil Corporation, New York, N.Y.

[21] Appl. No.: 794,328

[22] Filed: Nov. 4, 1985

Related U.S. Application Data

[63] Continuation of Ser. No. 726,193, Apr. 22, 1985, abandoned.

[51] Int. Cl.$^4$ ............................................... C07C 12/02
[52] U.S. Cl. ..................................... 585/517; 585/515
[58] Field of Search ................................ 585/415, 417

[56] References Cited

U.S. PATENT DOCUMENTS 4,490,569 12/1984 Chu et al. ............................ 585/415

Primary Examiner—Curtis R. Davis
Attorney, Agent, or Firm—Alexander J. McKillop; Michael G. Gilman; Edward F. Kenehan, Jr.

[57] ABSTRACT

There is provided a catalyst comprising (i) ZSM-5 or ZSM-11, (ii) gallium and (iii) thorium. Also provided is a process for converting ethylene, propylene and/or propane into aromatics with this catalyst. Modification of ZSM-5 with both Ga and Th has been found to result in greater yields of liquid and BTX from a refinery off gas stream than can be obtained with ZSM-5 modified only with Ga.

12 Claims, No Drawings

AROMATIZATION CATALYST FOR A REFINERY OFF GAS STREAM

This is a continuation of copending application Ser. No. 726,193, filed on Apr. 22, 1985, and now abandoned.

BACKGROUND

The present invention relates to catalysts comprising (i) ZSM-5 or ZSM-11, (ii) gallium and (iii) thorium and to aromatization reactions conducted therewith.

The Chester et al U.S. Pat. No. 4,350,835 describes a process for converting ethane to liquid aromatics by contacting the ethane with a zeolite catalyst such as ZSM-5 having incorporated therein a minor amount of gallium.

The Davies et al U.S. Pat. No. 4,175,057 describes a process for producing aromatics by contacting a $C_3$-$C_8$ hydrocarbon with a gallium catalyst supported on an aluminosilicate in which the ratio of silica to alumina is between 20:1 and 70:1.

The Bulford et al U.S. Pat. No. 4,157,356 describes a process for producing aromatic hydrocarbons by contacting a $C_3$-$C_8$ hydrocarbon with a gallium catalyst on a silica support which has a surface area greater than 500 $m^2/g$ and a pore volume less than 0.8 ml/g.

The Chu U.S. Pat. No. 4,276,437 describes a zeolite catalyst such as ZSM-5 having been modified by treatment with a compound of gallium to deposit thereon a minor proportion of this element on the zeolite. Also, the Chu U.S. Pat. No. 4,302,622 describes a similarly modified zeolite catalyst, wherein the gallium modifier is replaced by a Group IIIA element modifier. The catalysts of these Chu patents are described as being capable of converting aromatic compounds to dialkylbenzene compounds rich in the para-isomer.

The entire disclosures of the above-mentioned U.S. Patents are expressly incorporated herein by reference.

SUMMARY

According to one aspect of the present invention, there is provided a catalyst comprising (i) a zeolite having the structure of ZSM-5 or ZSM-11, (ii) gallium and (iii) thorium.

According to another aspect of this invention, there is provided a process for converting a feedstock to aromatic compounds, said feedstock comprising one or more of ethylene, propylene, and propane, said process comprising contacting said feedstock under sufficient aromatization conditions with an aromatization catalyst, said aromatization catalyst comprising (i) a zeolite having the structure of ZSM-5 or ZSM-11, (ii) gallium and (iii) thorium.

Modification of ZSM-5 with both Ga ad Th results in greater yields of liquid and BTX from a refinery off gas stream than can be obtained with ZSM-5 modified only with Ga. In view of the structural similarities between ZSM-5 and ZSM-11, it would be reasonable to predict that analogous results would be observed for such modification of ZSM-11.

EMBODIMENTS

ZSM-5 and ZSM-11 are known to be microporous crystalline zeolite structures having characteristic X-ray diffraction patterns.

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a larger number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties.

Such molecular sieves, both natural and synthetic, include a wide variety of positive ion-containing crystalline aluminosilicates. These aluminosilicates can be described as a rigid three-dimensional framework of $SiO_4$ and $AlO_4$ in which the tetrahedra are cross-linked by the sharing of oxygen atoms whereby the ratio of the total aluminum and silicon atoms to oxygen atoms is 1:2. The electrovalence of the tetrahedra containing aluminum is balanced by the inclusion in the crystal of a cation, for example an alkali metal or an alkaline earth metal cation. This can be expressed wherein the ratio of aluminum to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given aluminosilicate by suitable selection of the cation. The spaces between the tetrahedra are occupied by molecules of water prior to dehydration.

Although zeolites may contain silica and alumina, it is recognized that the silica and alumina portions may be replaced in whole or in part with other oxides. More particularly, $GeO_2$ is an art recognized substitute for $SiO_2$ and $B_2O_3$, $Cr_2O_3$, $Fe_2O_3$, and $Ga_2O_3$ are art recognized replacements for $Al_2O_3$. Accordingly, the term zeolite as used herein shall connote not only materials containing silicon and, optionally, aluminum atoms in the crystalline lattice structure thereof, but also materials which contain suitable replacement atoms for such silicon and/or aluminum. On the other hand, the term aluminosilicate zeolite as used herein shall define zeolite materials consisting essentially of silicon and, optionally, aluminum atoms in the crystalline lattice structure thereof, as opposed to materials which contain substantial amounts of suitable replacement atoms for such silicon and/or aluminum.

ZSM-5 is described in U.S. Pat. Nos. 3,702,886 and Re. 29,948. The entire descriptions contained within those patents, particularly the X-ray diffraction pattern of therein disclosed ZSM-5, are incorporated herein by reference.

Large crystal size ZSM-5 may be made in accordance with a procedure set forth in the Dwyer et al U.S. Pat. No. 4,375,458, the entire disclosure of which is expressly incorporated herein by reference. Small crystal size ZSM-5, more particularly microcrystalline ZSM-5 (e.g., 0.02–0.05 microns), may be made in accordance with a procedure set forth in the Dwyer et al U.S. Pat. No. 4,441,991, the entire disclosure of which is also expressly incorporated herein by reference.

ZSM-11 is described in U.S. Pat. No. 3,709,979. That description, and in particular the X-ray diffraction pattern of said ZSM-11, is incorporated herein by reference.

The aluminosilicate form of the zeolite catalyst component of the present invention may have a molar ratio of silica to alumina of, e.g., at least 12, i.e. from 12 to infinity.

The gallium and thorium in the catalyst may be present as oxides and/or as cations. For example, cations of the zeolite may be exchanged for gallium ions, whereby gallium ions are provided as an aqueous solution of gallium salts, such as, e.g., gallium nitrate, gallium chloride or gallium sulphate. Gallium exchanged zeolites may be produced by conventional ion exchange techniques and the ion exchanged zeolites so produced are subsequently dried. For example, an aqueous solution of a gallium compound such as gallium nitrate may be placed in contact with the zeolite at ambient or elevated temperature, e.g. by refluxing. The exchanged zeolite is then separated by decantation followed by filtration, washed several times with deionised water and finally dried. Before addition to the aqueous solution of the gallium compound, the zeolite may be acid treated. Zeolites may be exchanged with thorium by similar procedures.

The process of the present invention may also be carried out using catalysts in which gallium (or thorium) is only impregnated on the surface of the zeolite or is incorporated in the intracrystalline zeolite cavities as a gallium (or thorium) compound which gives rise to gallium (or thorium) oxide during activation of the catalyst prior to contact with the feedstock.

Zeolites may be contacted with a variety of solutions of gallium and thorium compounds in order to incorporate these elements on the zeolites.

Solutions of such compounds may be in any suitable solvent which is inert with respect to the metal-containing compound and the zeolite. Non-limiting examples of some suitable solvents include water, aliphatic and aromatic hydrocarbons, alcohols, organic acids (such as acetic acid, formic acid, propionic acid and so forth), and inorganic acids (such as hydrochloric acid, sulfuric acid and nitric acid). Other commonly available solvents such as halogenated hydrocarbons, ketones, ethers, etc. may be useful to dissolve some metal compounds or complexes. Generally, the most useful solvent will be found to be water. However, the solvent of choice for any particular compound will, of course, be determined by the nature of that compound and for that reason the foregoing list should not be considered exhaustive of all of the suitable possibilities.

Representative gallium-containing compounds include gallium acetate, gallium acetylacetonate, gallium bromide, gallium chloride, gallium fluoride, gallium iodide, gallium nitrate, gallium oxide, gallium sulfate and gallium sulfide. This listing is not to be taken as encompassing all of the utilizable gallium-containing compounds. It is merely intended to be illustrative of some of the representative metal compounds which those in the art will find useful in practicing the disclosed invention. The knowledgeable reader will readily appreciate that there are numerous other known gallium salts and complexes which would prove useful herein to provide solutions containing gallium suitable for combination with the zeolite in the manner hereinafter described. It will further be appreciated that a variety of thorium-containing compounds may be used for incorporating thorium on the zeolites.

Reaction of the zeolites with the treating compound (i.e., gallium or thorium compound) is effected by contacting the zeolites with such compound. Where the treating compound is a liquid, such compound can be in solution in a solvent at the time contact with the zeolite is effected. Any solvent relatively inert with respect to the treating compound and the zeolite may be employed. Suitable solvents include water and aliphatic, aromatic or alcoholic liquid. The treating compound may also be used without a solvent, i.e., may be used as a neat liquid. Where the treating compound is in the gaseous phase, it can be used by itself of in admixture with a gaseous diluent relatively inert to the treating compound and the zeolite (such as helium or nitrogen) or with an organic solvent such as octane or toluene. Heating of the treating compound impregnated catalyst subsequent to preparation and prior to use is preferred, and such heating can, if desired, be carried out in the presence of oxygen-for example, in air. Although heating may be carried out at a temperature of about 150° C. or more, higher temperatures, e.g., up to about 500° C., are preferred. Heating is generally carried out for 1–5 hours but may be extended to 24 hours or longer. While heating temperatures above about 500° C. may be employed, they are generally not necessary, and at temperatures of about 1000° C. the crystal structure of ZSM-5 tends to deteriorate. After heating in air at elevated temperatures, and without being limited by any theoretical considerations, it is contemplated that the gallium and thorium is actually present in the zeolite in an oxidized state, e.g., $Ga_2O_3$.

The amount of the gallium in the catalyst may be, e.g., from about 0.05 to about 10 weight percent based upon the weight of the zeolite in the catalyst, and the amount of the thorium in the catalyst may be, e.g., from about 0.05 to about 10 weight percent based upon the weight of the zeolite in the catalyst.

When the catalyst comprises oxides of gallium and thorium, the catalyst may comprise, e.g., at least 0.1 weight percent of each of these oxides based upon the weight of the zeolite in the catalyst.

Particularly when an impregnation process is used in order to incorporate oxides of gallium and/or thorium onto the zeolite, these oxides may partially block the pore space of the zeolite.

The weight percent of gallium in the zeolite may be, e.g., from about 0.1 to about 10 times the weight percent of the thorium in the catalyst.

It may be useful to incorporate the gallium/thorium modified zeolite with a matrix comprising another material resistant to the temperature and other conditions employed in the process. Such matrix material is useful as a binder and imparts greater resistance to the catalyst for the severe temperature, pressure and reactant feed stream velocity conditions encountered in many cracking processes.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is haloysite, kaolinite, dickite, nacrite or anauxite. Such clays can be used in the raw state as originally mined or initially subjected to calcination, acid treatment or chemical modification.

In addition to the foregoing materials, modified zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportion of modified zeolite component and inorganic oxide gel matrix on an anhydrous basis, may vary widely with the modified zeolite content ranging from between about 1 to about 99 percent by weight and more usually in the range of about 5 to about 80 percent by weight of the dry composite.

The aromatization conditions suitable for use in accordance with the present invention may include, e.g., a temperature of from about 100° C. to about 700° C., a pressure of from about 0.1 atmosphere to about 60 atmospheres, a weight hourly space velocity (WHSV) of from about 0.1 to about 400 and a hydrogen/hydrocarbon mole ratio of from about 0 to about 20.

The feedstock to be aromatized may comprise, e.g., from about 1 to about 30 weight percent of ethylene, from about 1 to about 30 weight percent of propylene and from about 1 to about 30 weight percent of propane. This feedstock may be, e.g., a refinery off gas.

A catalyst composed of 2 wt% gallium and 1 wt% thorium impregnated on ZSM-5 zeolite was found to convert ethylene, propylene and propane in high yields to aromatics from a refinery off gas stream.

EXAMPLE 1

A large crystal size ZSM-5 aluminosilicate zeolite was prepared substantially in accordance with the method of Example 1 of the Dwyer et al U.S. Pat. No. 4,375,458 or equivalent procedure. This large crystal size ZSM-5 had a $SiO_2:Al_2O_3$ ratio of about 70:1. This ZSM-5 was then composited with an alumina binder in the form of an extrudate containing 65 wt. percent ZSM-5 and 35 wt. percent alumina binder.

A 5 g portion of the ammonium exchanged form of this ZSM-5 extrudate, i.e., $NH_4ZSM-5$, was impregnated with 10 ml of $H_2O$ containing 0.60 g of $Ga(NO_3)_3.9H_2O$ and 0.12 g of $Th(NO_3)_4.4H_2O$. This was dried and then calcined in air for 16 hours at 525° C. The resulting catalyst contained 2 wt% of gallium and 1 wt% of thorium.

COMPARATIVE EXAMPLE A

HZSM-5

10 g of a large crystal size ZSM-5 extrudate, prepared in accordance with the procedure of Example 1, in as-synthesized form, were calcined under an atmosphere of $N_2$ at 500° C. for 6 hours to form NaZSM-5. This was then exchanged with a 0.5N solution of $NH_4NO_3$ to remove the Na and form $NH_4ZSM-5$. This was dried at 100° C. and then calcined under air at 525° C. for 16 hours to form HZSM-5. 5 g were used for the aromatization experiment described in Example 2.

COMPARATIVE EXAMPLE B

GaHZSM-5

5 g of $NH_4ZSM-5$ extrudate, prepared in accordance with the procedure of Example 1, were impregnated with 10 ml of $H_2O$ containing 0.30 g of $Ga(NO_3)_3.9H_2O$. This was evaporated to dryness at 100° C. and then calcined under air at 525° C. for 16 hours. The resulting modified extrudate contained 1.00% by weight Ga.

COMPARATIVE EXAMPLE C

ThHZSM-5

5 g of $NH_4ZSM-5$ extrudate, prepared in accordance with the procedure of Example 1, were immersed in 10 ml of $H_2O$ containing 0.06 g of $Th(NO_3)_3.4H_2O$ and evaporated to dryness at 100° C. The dry material was then calcined under air at 525° C. for 16 hours to form ThHZSM-5 containing 0.50% by weight Th.

EXAMPLE 2

A gaseous feed composed of $H_2$-1.2 wt%, $CH_4$-38.8 wt%, $C_2H_6$-30.8 wt%, $C_2H_4$-18.5 wt%, $C_3H_8$-2.0 wt% and $C_3H_6$-8.7 wt% was fed over the catalysts of Example 1 and Comparative Examples A-C at equivalent reaction conditions. Table 1 summarizes the results obtained.

TABLE 1

| | Aromatization of Refinery Off Gas | | | |
|---|---|---|---|---|
| Catalyst: | HZSM-5 | GaHZSM-5 | ThHZSM-5 | GaThHZSM-5 |
| Temp., °C. | 550 | 550 | 550 | 550 |
| WHSV | 0.5 | 0.5 | 0.5 | 0.5 |
| Pressure | atmos | atmos | atmos | atmos |
| Wt % | | | | |
| Benzene | 28.2 | 31.9 | 20.3 | 39.5 |
| Toluene | 40.4 | 39.1 | 38.7 | 38.8 |
| $C_8$— Arom. | 19.9 | 17.5 | 25.3 | 11.0 |
| $C_9$— Arom. | 7.4 | 4.2 | 10.6 | 2.0 |
| $C_9+$ Arom. | 4.1 | 7.3 | 5.1 | 8.7 |
| % of Aromatizable $C_2^=C_3^=C_3^•$ Converted To: | | | | |
| Liquid: | 58.3 | 62.7 | 49.3 | 69.5 |
| BTX: | 51.6 | 55.5 | 41.5 | 62.1 |

Surprisingly and unexpectedly, it was found that combining Ga and Th resulted in a catalyst that produced appreciably more liquid and BTX (i.e., a combination of benzene, toluene, xylene and ethylbenzene) from this gaseous feed than did the comparative catalysts.

EXAMPLE 3

A catalyst composed of 1 wt% gallium and 0.5 wt% thorium impregnated on ZSM-5 was prepared as follows. 5 g of the $NH_4ZSM-5$ extrudate referred to in Example 1 were immersed in 10 ml of $H_2O$ containing 0.30 g of $Ga(NO_3)_3.9H_2O$ and 0.06 g of $Th(NO_3)_3.4H_2O$ and evaporated to dryness at 100° C. This was calcined under air at 525° C. for 16 hours to form GaThHZSM-5 containing 1.00 wt. % Ga and 0.50 wt. % Th.

EXAMPLE 4

A simulated, refinery off gas feed containing 32–33 wt% olefins was fed over the catalyst of Example 3 as well as an unmodified version thereof. Table 2 summarizes the results obtained.

EXAMPLE 5

A catalyst composed of 1 wt% gallium and 0.5 wt% thorium impregnated on ZSM-5 was prepared as follows. A microcrystalline ZSM-5 aluminosilicate zeolite was prepared by a method substantially in accordance with Example A of the Dwyer et al U.S. Pat. No. 4,441,991 or equivalent procedure. This microcrystalline ZSM-5 had a $SiO_2:Al_2O_3$ ratio of about 70:1. This ZSM-5 was composited with an alumina binder in the form of an extrudate containing 65 wt. percent ZSM-5 and 35 wt. percent alumina binder.

5 g of this extrudate, in the $NH_4ZSM$-5 form, were treated as in Example 3 to form a catalyst containing 1.00 wt. % Ga and 0.50 wt. % Th.

EXAMPLE 6

A simulated, refinery off gas feed containing 32-33 wt% olefins was fed over the catalyst of Example 5 as well as an unmodified version thereof. Table 3 summarizes the results obtained.

Tables 2 and 3 compare Ga-Th modified ZSM-5 catalysts with their unmodified counterparts. For conditions under which catalyst aging was insignificant, only averaged data for the TOS (i.e., time on stream) intervals are shown.

Irrespective of the crystal size, impregnation with Ga and Th increases the aromatization activity and selectivity to BTX of the extrudates. At approximately the same olefin conversion as their corresponding unmodified extrudates both modified zeolites make more BTX, less heavies, less methane, and less ethane. The modified zeolites age faster than the unmodified ones, particularly at the higher temprature (600° C.) and higher pressure (50 psig).

TABLE 2

Simulated, Refinery, Off-Gas Aromatization Effect of Ga—Th Impregnation on ZSM-5

| | Ga—Th ZSM-5 | | | | | | | | Unmodified ZSM-5 | | | | |
|---|---|---|---|---|---|---|---|---|---|---|---|---|---|
| Temp., °C. | 550 | 550 | 600 | 600 | 550 | 550 | 550 | 550 | 550 | 600 | 600 | 550 | 550 |
| Press., psig | 0 | 0 | 0 | 0 | 50 | 50 | 0 | 0 | 0 | 0 | 0 | 50 | 50 |
| Contact Time, sec. | 3 | 3 | 3 | 3 | 6 | 6 | 3 | 6 | 12 | 6 | 6 | 6 | 6 |
| WHSV | 0.5 | 0.5 | 0.5 | 0.5 | 1.1 | 1.1 | 0.5 | 0.25 | 0.125 | 0.25 | 0.25 | 1.1 | 1.1 |
| TOS, hr. | 3 | 0–21 | 30 | 30–40 | 3 | 0–18 | 0–10 | 20–25 | 27 | 29 | 29–44 | 3 | 0–24 |
| Liquid Yield, % | 20.3 | 19.9 | 17.3 | 9.2 | 17.8 | 13.4 | 16.1 | 17.4 | 17.7 | 17.1 | 15 | 13.6 | 9.5 |
| BTX Yield, % | 18.7 | 18.3 | 15.5 | 8.2 | 16.4 | 11.9 | 14.6 | 15.6 | 15.5 | 14.7 | 13 | 12.2 | 8.0 |
| Wt % BTX in Liq. | 92.4 | 92.1 | 89.7 | 87.4 | 92.0 | 87.5 | 90.8 | 89.9 | 87.7 | 86 | 87.3 | 89.5 | 73.4 |
| Benzene/toluene | 1.0 | 0.99 | 1.2 | 1.04 | 0.8 | 0.7 | 0.62 | 0.79 | 1.04 | 1.66 | 1.3 | 0.47 | 0.46 |
| BTX Yield from Olefins, % | 56 | 54.8 | 46.4 | 24.6 | 49.1 | 35.6 | 43.7 | 46.7 | 46.4 | 44 | 38.9 | 37.8 | 24.8 |
| Conversion | | | | | | | | | | | | | |
| $C_2=$ | 89 | 87 | 71 | 40 | 84 | 65 | 75 | 80 | 85 | 79 | 68 | 78 | 58 |
| $C_3=$ | 96 | 95 | 92 | 64 | 92 | 80 | 87 | 92 | 96 | 96 | 90 | 82 | 62 |
| $C_3°$ | 37 | 27 | 50 | 19 | −23 | −23 | −10 | 12 | 43 | 78 | 50 | −41 | −31 |
| $C_1$ | −17 | −16 | −17 | −11 | −13 | −10 | −13 | −16 | −20 | −25 | −21 | −10 | −6 |
| $C_2°$ | −25 | −24 | −24 | −17 | −19 | −17 | −17 | −22 | −28 | −26 | −24 | −14 | −11 |

TABLE 3

Simulated, Refinery, Off-Gas Conversion Effect of Ga—Th Impregnation on ZSM-5

| | Ga—Th ZSM-5 | | | | | | | | | |
|---|---|---|---|---|---|---|---|---|---|---|
| Temp., °C. | 550 | 550 | 550 | 550 | 600 | 600 | 550 | 550 | 600 | 600 |
| Press., psig | 0 | 0 | 0 | 0 | 0 | 0 | 50 | 50 | 50 | 50 |
| Contact Time, sec. | 3.7 | 3 | 2.2 | 2.2 | 2.2 | 2.2 | 2.2 | 2.2 | 2.2 | 2.2 |
| TOS, hr. | 2–4 | 6 | 12 | 7–27 | 29.5 | 28–48 | 3 | 0–25 | 28.3 | 28.5–44 |
| Liquid Yield, % | 21.7 | 21.9 | 21.6 | 21.1 | 20.5 | 15.5 | 20.2 | 19.1 | 18.6 | 15.1 |
| BTX Yield, % | 19.3 | 19.6 | 19.2 | 18.7 | 17.7 | 13.5 | 17.9 | 16.9 | 16.3 | 13.1 |
| Wt % BTX in Liq. | 88.9 | 89.3 | 89.2 | 88.4 | 86.4 | 87.1 | 88.7 | 88.4 | 87.7 | 86.3 |
| Benzene/toluene | 1.20 | 1.1 | 1.0 | 0.96 | 1.38 | 1.12 | 0.75 | 0.71 | 0.92 | 0.76 |
| BTX Yield from Olefins, % | 59.8 | 60.8 | 59.5 | 58 | 54.9 | 41.9 | 55.5 | 52.4 | 50.5 | 40.6 |
| Conversion | | | | | | | | | | |
| $C_2=$ | 92 | 91 | 90 | 89 | 83 | 63 | 91 | 92 | 91 | 79 |
| $C_3=$ | 98 | 97 | 96 | 95 | 95 | 83 | 96 | 96 | 96 | 85 |
| $C_3°$ | 66 | 57 | 39 | 30 | 73 | 34 | −10 | −16 | 96 | 22 |
| $C_1$ | −18 | −16 | −13 | −12 | −16 | −12 | −18 | −13 | −17 | −12 |
| $C_2°$ | −19 | −19 | −18 | −18 | −21 | −18 | −14 | −18 | −18 | −23 |

| | Unmodified ZSM-5 | | | | | | | |
|---|---|---|---|---|---|---|---|---|
| Temp., °C. | 550 | 550 | 550 | 600 | 600 | 550 | 600 | 600 |
| Press., psig | 0 | 0 | 0 | 0 | 0 | 50 | 50 | 50 |
| Contact Time, sec. | 3.7 | 6 | 12 | 6 | 6 | 6 | 6 | 6 |
| WHSV | 0.4 | 0.25 | 0.125 | 0.25 | 0.25 | 1.1 | 1.1 | 1.1 |
| TOS, hr. | 0–24 | 24–40 | 40–52 | 53 | 52–71 | 0–26 | 29 | 26–50 |
| Liquid Yield, % | 17.5 | 18.7 | 19 | 18.8 | 17.4 | 16.4 | 17.9 | 17.7 |
| BTX Yield, % | 15.6 | 16.5 | 15.9 | 15.5 | 14.5 | 14 | 15.4 | 15.2 |
| Wt % BTX in Liq. | 89.4 | 88.3 | 84 | 82.3 | 83.1 | 85.7 | 85.8 | 86.2 |
| Benzene/toluene | 0.82 | 1.0 | 1.38 | 2.2 | 1.82 | 0.75 | 1.2 | 1.12 |
| BTX Yield from Olefins, % | 48.6 | 49.4 | 47.6 | 46.4 | 43.4 | 41.9 | 46.1 | 45.5 |
| Conversions | | | | | | | | |
| $C_2=$ | 78 | 85 | 90 | 86 | 81 | 94 | 94 | 93 |
| $C_3=$ | 91 | 95 | 97 | 97 | 96 | 97 | 98 | 97 |
| $C_3°$ | 15 | 30 | 61 | 88 | 73 | 13 | 85 | 71 |
| $C_1$ | −15 | −19 | −24 | −29 | −26 | −24 | −31 | −28 |
| $C_2°$ | −16 | −23 | −27 | −24 | −26 | −30 | −35 | −35 |

From among the two modified zeolites, the catalyst of Example 5 appears to be better than the catalyst of Example 3. The catalyst of Example 5 is more active, and it makes less non-aromatizable light hydrocarbons. It also ages more slowly than the catalyst of Example 3, as can be seen by averaged data at that condition. It is inferior to the catalyst of Example 3 only in that it makes more $C_9+$.

What is claimed is:

1. A process for converting a feedstock to aromatic compounds, said feedstock comprising one or more of ethylene, propylene and propane, said process comprising contacting said feedstock under sufficient aromatization conditions with an aromatization catalyst, said aromatization catalyst comprising (i) a zeolite having the structure of ZSM-5 or ZSM-11, (ii) gallium and (iii) thorium.

2. A process according to claim 1, wherein the amount of said gallium in said catalyst is from about 0.05 to about 10 weight percent based upon the weight of said zeolite and the amount of said thorium in said catalyst is from about 0.05 to about 10 weight percent based upon the weight of said zeolite.

3. A process according to claim 1, wherein said gallium and said thorium (i) occupy cation exchange sites on said zeolite and/or (ii) are in the form of oxides thereof.

4. A process according to claim 3, wherein said catalyst comprises at least 0.1 weight percent of gallium oxide based upon the weight of said zeolite and at least 0.1 weight percent of thorium oxide based upon the weight of said zeolite.

5. A process according to claim 4, wherein said gallium oxide and said thorium oxide are incorporated into said catalyst by an impregnation process followed by calcination, whereby the pores of said zeolite become partially blocked by said gallium oxide and/or thorium oxide.

6. A process according to claim 5, wherein the weight percent of gallium in said catalyst is about twice the weight percent of thorium in said catalyst.

7. A process according to claim 6, wherein said catalyst has 2 weight percent of gallium based upon the weight of said zeolite and 1 weight percent of thorium based upon the weight of said zeolite.

8. A process according to claim 1 wherein said catalyst further comprises a binder.

9. A process according to claim 1, wherein said aromatization conditions include a temperature of from about 100° C. to about 700° C., a pressure of from about 0.1 atmosphere to about 60 atmospheres, a weight hourly space velocity (WHSV) of from about 0.1 to about 400 and a hydrogen/hydrocarbon mole ratio of from about 0 to about 20.

10. A process according to claim 1, wherein said feedstock comprises from about 1 to about 30 weight percent of ethylene, from about 1 to about 30 weight percent of propylene and from about 1 to about 30 weight percent of propane.

11. A process according to claim 1, wherein said feedstock is a refinery off gas.

12. A process according to claim 1, wherein said zeolite is an aluminosilicate zeolite having the structure of ZSM-5.

* * * * *